United States Patent [19]

Dai et al.

[11] Patent Number: 5,453,536

[45] Date of Patent: Sep. 26, 1995

[54] POLYCARBAMATES, PROCESS FOR PREPARING POLYCARBAMATES, AND PROCESS FOR PREPARING POLYISOCYANATES

[75] Inventors: Shenghong A. Dai; Chester R. Norman; Hong-Anh Nguyen, all of Lake Jackson, Tex.

[73] Assignee: The Dow Chemical Company, Midland, Mich.

[21] Appl. No.: 209,151

[22] Filed: Mar. 10, 1994

[51] Int. Cl.[6] .................. C07C 261/00; C07C 263/00
[52] U.S. Cl. ............................... 560/345; 560/25
[58] Field of Search .......................... 560/25, 345

[56] References Cited

U.S. PATENT DOCUMENTS

| | | | |
|---|---|---|---|
| 3,234,253 | 2/1986 | Cooper | 260/453 |
| 4,290,968 | 9/1981 | Leonard | 560/345 |
| 4,487,713 | 12/1984 | Spohn | 560/345 |

OTHER PUBLICATIONS

Chin, "New Nonphosgenation Process for MDI by Asahi Chemical Industry" Mar. 1984, Process Economics Program, SRI International, Menlo Park, Calif., 94025, pp. 1–32.

Fukuoka et al. "Isocyanate Without Phosgene", *Chemtech*, Nov. 1984, pp. 670–676.

SRI Process Evaluation/Reserach Planning Report, 86–T–3, "2.00 A New Process for Methylene Diphenyl Diisocyanate", 1986, pp. 27–58.

*Primary Examiner*—Arthur C. Prescott

[57] ABSTRACT

Polycarbamates of a polyisocyanate and secondary alcohols are disclosed. These carbamates are characterized in being readily pyrolyzed to form the corresponding polyisocyanate and alcohol with low formation of tars and other by-products. Thus, these polycarbamates can be pyrolyzed under relatively mild conditions, and in the absence of solvent and catalyst.

19 Claims, No Drawings

POLYCARBAMATES, PROCESS FOR PREPARING POLYCARBAMATES, AND PROCESS FOR PREPARING POLYISOCYANATES

BACKGROUND OF THE INVENTION

This invention relates to a process for preparing polyisocyanates such as are useful, for example, in making polyurethane polymers.

Polyisocyanates are commonly used in various applications, the most common of which is the preparation of polyurethane polymers. The most commercially important of these are aromatic polyisocyanates such as toluene diisocyanate (TDI), diphenylmethane diisocyanate (MDI) and the so-called polymeric MDI products which are usually formed as by-products in MDI production. However, certain aliphatic polyisocyanates are also used commercially, such as hexamethylene diisocyanate, isophorone diisocyanate and hydrogenated MDI ($H_{12}$ MDI).

On a commercial scale, polyisocyanates are almost universally produced by reacting the corresponding polyamine with phosgene. For example, TDI is produced by reacting phosgene with toluene diamine. Several problems are associated with this process, the most significant of which is that large quantities of phosgene must be handled. Phosgene is highly toxic, and its handling requires special care to prevent exposure to workers. HCl is produced in the reaction of the phosgene and the polyamine, and must be neutralized or otherwise removed. The phosgene and HCl also engage in various side reactions, producing unwanted chlorinated by-products which affect the quality and purity of the product polyisocyanates. Thus, a process by which polyisocyanates can be prepared without using phosgene would be highly desirable.

Several non-phosgene routes to polyisocyanates have been developed. One such route involves the preparation of an n-alkyl biscarbamate, which is subsequently pyrolyzed to form the corresponding polyisocyanate and alcohol. The biscarbamate is generally prepared by one of two methods. The first such method involves the oxidative carbonylation of an amine with carbon monoxide, oxygen and an alcohol such as ethanol or methanol, to form the corresponding ethyl- or methylcarbamate. The other method involves a reductive carbonylation of a nitro compound with carbon monoxide and an alcohol such as ethanol or methanol to form the corresponding ethyl- or methylcarbamate. See, e.g., WO 86-05179.

In these processes, the ethyl- or methylpolycarbamates are pyrolyzed at high temperatures and under reduced pressures. At these temperatures, the polyisocyanates often polymerize as they form, producing tars and other by-products. For this reason, and because these carbamates are often crystalline, a solvent is required as a diluent. The use of a solvent in the pyrolysis adds costs in recovering the product polyisocyanate from the solvent. To a lesser extent, the high temperature required further increases the cost of these processes.

Thus, it would be desirable to provide a route to make polyisocyanates through a polycarbamate intermediate, wherein the pyrolysis of the polycarbamate can be conducted in the absence of solvent, and preferably at moderate temperatures.

SUMMARY OF THE INVENTION

In one aspect this invention is a polycarbamate as represented by the structure (I)

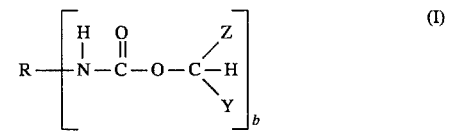

wherein b is a number of two or more, R is an organic radical with a valence equal to b, Y is a group having at least two carbon atoms, and Z is an aliphatic or aromatic group containing at least one carbon atom.

In another aspect, this invention is a process for preparing a polyisocyanate, comprising pyrolyzing the polycarbamate of the first aspect under reduced pressure and at a temperature of about 150° to about 270° C., to form the corresponding polyisocyanate and alcohol.

In a third aspect, this invention is a process for preparing a polyisocyanate, comprising forming a polycarbamate of the first aspect, and then pyrolyzing the polycarbamate under reduced pressure and at a temperature of about 150° to about 270° C., to form the corresponding polyisocyanate and alcohol.

In a fourth aspect, this invention is a process for preparing a polycarbamate comprising reacting a polycarbamate represented by the structure (II)

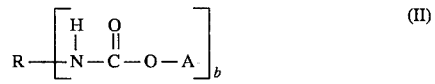

wherein A is $C_{1-6}$ linear alkyl with a secondary alcohol represented by the structure Z—CH(OH)—Y, at an elevated temperature such that the polycarbamate represented by structure (I) and an alcohol of the structure A—OH are formed, and wherein the alcohol A—OH is removed from the product polycarbamate continuously or intermittently as it forms.

Unexpectedly, the polycarbamate of this invention can be pyrolyzed to form the corresponding polyisocyanate under surprisingly mild conditions, compared to those required to pyrolyze ethyl- or methylpolycarbamates. Thus, the pyrolysis can be conducted at lower temperatures than required to pyrolyze ethyl- or methylpolycarbamate, and also can be conducted neat and without solvent. In addition, the polycarbamates can be pyrolyzed in the substantial absence of solvent with greatly reduced formation of tar and other by-products, compared to those formed in the neat pyrolysis of ethyl- or methylpolycarbamates. Since no solvents are needed, the isolation of the isocyanate and the alcohol can be greatly simplified.

DETAILED DESCRIPTION OF THE INVENTION

The polycarbamate of this invention is a compound represented by the structure

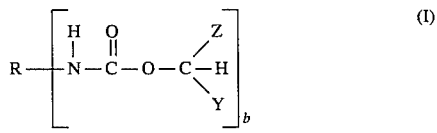

wherein b is a number of two or more, R is a organic radical with a valence equal to b, Y is a a group having at least two carbon atoms, and Z is an aliphatic or aromatic group containing at least one carbon atom.

In structure (I), "b" is preferably a number from about two to about four, more preferably from about two to about three, most preferably about two.

"R" is preferably a hydrocarbon radical, which may be aliphatic, alicyclic, or aromatic. Suitable aliphatic hydrocarbon radicals include straight chain or branched hydrocarbons having from about two, preferably from about 4 carbon atoms to about 20, preferably about 12, more preferably about 8 carbon atoms. Most preferred are linear hydrocarbon diradicals having from 4 to 8 carbon atoms. Examples of such include tetramethylene, pentamethylene, hexamethylene, and octamethylene diradicals. Suitable alicyclic hydrocarbon radicals include monocyclic and polycyclic hydrocarbons, preferably monocyclic hydrocarbons having from about 6 to about 16 carbon atoms. Among these preferred alicyclic hydrocarbon radicals are cyclohexane, alkyl-substituted cyclohexane, isophorone dialkyl-substituted cyclohexane, mono- or dihalo-substituted cyclohexane, cyclooctane, alkyl-substituted cyclooctane, dialkyl-substituted cyclooctane, mono- or dihalo-substituted cyclooctane, bis-(cyclohexyl)alkanes such as methylene bis(cyclohexane) and propylidene bis(cyclohexane), and like radicals. Suitable aromatic polyradicals include polyradicals of benzene, toluene and other monoalkyl benzenes, o-, p-, and m-xylene and other dialkyl benzenes, diphenylalkanes such as diphenyl methane and 2,2-diphenylpropane, halogenated aromatics, and the like.

Most preferred R radicals are hexamethylene, phenylene, diphenylmethane, toluene, cyclohexane, xylenyl, methylcyclohexane, isophorone and dicyclohexylmethane radicals.

In structure (I), exemplary "Z" groups include linear or branched alkyl, cycloalkyl, alkoxy-substituted alkyl, benzyl, phenyl or other aromatic group, which may be substituted, and like groups. Preferred Z groups include $C_1$–$C_4$ straight chain alkyl, $C_3$–$C_6$ branched alkyl, alkyl ether, phenyl, benzyl, and the like. More preferably, the Z group is methyl, ethyl, $C_3$–$C_6$ secondary alkyl, $C_4$–$C_6$ tertiary alkyl, phenyl or benzyl.

Exemplary Y groups include those having from about 2 to about 20, preferably about 3 to about 6 carbon atoms, and are represented by the structure

wherein $R^1$ and $R^2$ are hydrogen, $C_1$–$C_6$ alkyl, aromatic, benzyl, alkoxy or phenoxy and $R^3$ is $C_1$–$C_6$ alkyl, aromatic, benzyl, alkoxy, phenoxy or dialkylamine. $R^1$ is preferably hydrogen, $C_1$–$C_6$ alkyl or phenyl. $R^2$ is preferably $C_1$–$C_6$ alkyl, phenyl or $C_1$–$C_4$ alkoxy. If $R^1$ and $R^2$ are both hydrogen, $R^3$ may be $C_1$–$C_6$ alkyl, phenyl, alkoxy, phenoxy or dialkylamine, but in that case it is preferred that $R^3$ is $C_1$–$C_4$ alkoxy or phenoxy, more preferably methoxy or ethoxy. Otherwise, $R^3$ is preferably $C_1$–$C_4$ alkyl, phenyl or $C_1$–$C_2$ alkoxy, more preferably methyl, ethyl, methoxy or ethoxy.

Of particular interest are Y groups in which $R^1$ and $R^2$ are hydrogen and $R^3$ is ethoxy or methoxy; $R^1$ and $R^2$ are hydrogen and $R^3$ is methyl, ethyl or phenyl; $R^1$ is hydrogen and $R^2$ and $R^3$ are each methyl, ethyl or phenyl; $R^1$ is hydrogen, $R^2$ is methyl, ethyl or phenyl and $R^3$ is methoxy or ethoxy; $R^1$ and $R^2$ are both methyl, ethyl or phenyl and $R^3$ is methoxy or ethoxy; and $R^1$, $R^2$ and $R^3$ are all methyl or ethyl.

The polycarbamate of this invention can be prepared in a transesterification reaction involving a polycarbamate as represented by the structure

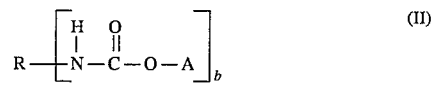

and an alcohol having the structure Z—CH(OH)—Y, wherein R, b, Y, and Z are as defined before and A is $C_1$–$C_4$ linear alkyl, preferably ethyl or methyl.

The transesterification reaction is conducted at an elevated temperature. In general, a temperature from about 50° to about 250° C. can be used, with faster reaction occurring at higher temperatures. As the reaction proceeds, an alcohol corresponding to the formula A—OH is produced. In order to drive the transesterification to completion, it is preferred to remove the alcohol A—OH from the product as the alcohol is formed. A simple way to accomplish this is to vent alcohol vapors. For this reason, it is preferred to conduct the reaction at a temperature above the boiling point of the alcohol A—OH.

The preferred temperature also depends on whether a catalyst is used to enhance the rate of the transesterification reaction. When a catalyst is used, it is preferred to use a moderate temperature, i.e. from about 50° to about 150° C. When no catalyst is used, a temperature of from about 100° to about 250° C. is preferred.

The transesterification reaction may be run in the presence of a diluent. The diluent advantageously has a boiling point in the temperature range at which the transesterification reaction is conducted, and the reaction is conducted under reflux conditions. The diluent may be any liquid in which the starting and product polycarbamates do not undesirably react. Suitable such diluents include aromatic solvents such as toluene and benzene, ethyl acetate, methylene chloride, acetone, and preferably the alcohol A—OH such as is formed during the transesterification reaction. Preferred solvents are those such as toluene, benzene and ethyl acetate which facilitate removal of the alcohol A—OH from the reaction mixture.

As mentioned before, a catalyst may be used in the transesterification reaction. Suitable catalysts include organometallic catalysts such as organotin, organotitanium, organomercury, organobismuth and similar compounds, with organotin compounds and titanium (IV) compounds being preferred. Suitable organotin compounds include those commonly employed as polyurethane catalysts, including, for example, tin octoate and dialkyl tin dialkanoates such as dimethyltin dilaurate and dibutyltin dilaurate. A suitable titanium (IV) compound is titanium (IV) isopropoxide. Conventional transesterification catalysts such as acids and bases can also be used. Exemplary acids include toluene sulfonic acid, sulfuric acid, and methanesulfonic acid. Exemplary bases include trialkyl amines and alkali metal alkoxides such as sodium or potassium methoxide.

The transesterification is conducted by contacting the polycarbamate starting material with the alcohol Z—CH(OH)—Y and heating them to a temperature as described above. An excess of the alcohol is preferably used in order to drive the reaction to completion. The catalyst, if used, is advantageously present in an amount from about 0.01 to about 5, preferably about 0.1 to about 1 weight percent, based on the weight of the starting polycarbamate. Product alcohol A—OH is preferably removed from the reaction mixture as it is formed, in order to drive the equilibrium towards the product polycarbamate. The alcohol Z—CH(OH)—Y can also be replenished as it is consumed, for the same reason. Depending on the temperature used, the reaction proceeds to 90 percent or higher yield in a period of about 1 to about 30 hours.

After the reaction, it is preferred to work up the product polycarbamate by stripping off volatile impurities and removing residual catalyst and starting polycarbamate though a suitable technique such as solvent extraction or recrystallization.

The starting polycarbamate can itself be prepared in an oxidative or reductive carbonylation of a polyamine of the formula R—NH2$_b$, wherein R and b are as defined before. Such processes are described, for example, in Japanese Patent (Kokai) Nos. 57-158746-48, 57-70855, 57-185253, and 57-188557. The oxidative carbonylation is advantageously carried out using carbon monoxide, oxygen and an ethanol (to make the polyethylcarbamate) or methanol (to make the polymethylcarbamate). The reductive carbonylation is advantageously carried out using carbon monoxide and methanol or ethanol, preferably in the presence of a ruthenium catalyst. In either case, the carbonylation is carried out at an elevated temperature and pressure in the presence of an excess of the methanol or ethanol.

A third process for preparing the starting polycarbamate is to oxidatively carbonylate a monoamine or reductive carbonylate a mononitro compound using ethanol or methanol to form a monocarbamate, followed by a coupling of the monocarbamate to form a polycarbamate. This method is particularly suitable for preparing polyaromatic carbamates. For example, a monocarbamate prepared from aniline or nitrobenzene can be coupled via condensation with an aldehyde or ketone to form an alkylene bis- or poly(phenyl carbamate). In such case, the monocarbamate is preferably the methyl or ethyl carbamate of aniline, and the ketone is preferably formaldehyde.

The polycarbamate of this invention can then be pyrolyzed to form the corresponding polyisocyanate. A significant advantage of this invention is that the pyrolysis of these polycarbamates is readily accomplished without the need for solvent or catalyst. In addition, the polycarbamates of this invention form fewer polymeric and tarry by-products upon pyrolysis than do corresponding n-alkyl polycarbamates.

The polycarbamates of this invention are advantageously decomposed into the corresponding polyisocyanate and alcohol by heating at a temperature from about 130° C., preferably from about 150° C., more preferably from about 175° C. up to about 300° C., preferably up to about 270° C., more preferably up to about 250° C., most preferably up to about 230° C. It is preferred to select a temperature at which the alcohol and the polyisocyanate, which are formed in the pyrolysis, are distilled as they are formed so that an equilibrium between the carbamate and polyisocyanate is not created. It is especially preferred that the temperature be such that both the alcohol and the polyisocyanate, which are formed in the reaction, distill from the reaction mixture as they are formed.

A subatmospheric pressure is preferred in the pyrolysis reaction, preferably from about 0.01 to 50 and especially from about 0.1 to about 5.0 torr, since that facilitates distillation of the alcohol and the polyisocyanate from the reaction mixture.

Although a solvent is not required during the pyrolysis step, one may be used if required. Any solvent can be used which dissolves the polycarbamate, is inert during the pyrolysis and is thermally stable at the temperature used in the pyrolysis reaction. Examples of such solvents include diphenyl oxide, alkylbenzenes, dialkylbenzenes, secondary alcohols, and the like.

In a preferred method, the polycarbamate is first heated to a relatively mild temperature, preferably about 50° up to about 100° C., and maintained at that temperature until the alcohol no longer distills off. This initial heating step is preferably done under vacuum. During this step, a polymeric residue often forms which is believed to contain allophanates and/or polyurethanes. This polymeric residue is then pyrolyzed at higher temperatures, as described above, to recover the polyisocyanate and additional alcohol. The resulting polyisocyanate can be distilled or otherwise purified if needed.

The polyisocyanate prepared in accordance with this invention is useful to prepare polyurethanes, polyureas, polyisocyanurates, polyamides, polyimides and like polymers. Process for preparing these types of polymers from polyisocyanates are well-known and described, for example, in U.S. Pat. Nos. 4,876,019, 4,929,646 and 5,010,117, all incorporated herein by reference.

EXAMPLES

The following examples are provided to illustrate the invention, but are not intended to limit the scope thereof. All parts and percentages are by weight unless otherwise indicated.

Example 1

Into a Parr reactor equipped with a vapor phase outlet and a liquid inlet are placed 31.47 parts diphenylmethane dimethyl biscarbamate (MDI dimethyl biscarbamate) and 200 parts 1-methoxy-2-propanol. The mixture is heated to about 220° C. with stirring to initiate the transesterification reaction. As the reaction proceeds, about 13 parts/hr of methanol-rich vapor phase is bled from the reactor, and about 13 parts/hr of 1-methoxy-2-propanol are added. After about 5 hours, the MDI dimethyl biscarbamate is totally consumed. The product mixture contains 93.4 percent of the MDI di(1-methoxy isopropyl) biscarbamate, and 5.6 percent of an MDI methyl(1-methyoxyisopropyl) biscarbamate.

Example 2

Into a suitable flask equipped with a condenser are placed 68.4 parts diphenylmethane diethyl biscarbamate (MDI diethyl biscarbamate), 180 parts 1-methoxy-2-propanol and 0.5 part dibutyltin dilaurate. The resulting mixture is heated to a temperature ranging from 125° to 145° C. Methanol is removed from the system as the reaction proceeds. After 72 hours, no MDI diethyl biscarbamate remains. The contents of the reaction flask are concentrated and 81.8 parts of MDI di(1-methoxy isopropanol) biscarbamate are obtained.

Example 3

Example 2 is repeated, except that the starting biscarbamate is 62.8 parts of MDI dimethyl biscarbamate. The product contains 80.3 parts of MDI di(1-methoxy isopropanol) biscarbamate.

Example 4

Example 2 is again repeated, this time substituting 0.9 g titanium (IV) isopropoxide for the dibutyltin dilaurate. After 72 hours reaction, 79.5 parts of MDI di(1-methoxy isopropanol) biscarbamate are obtained.

Example 5

Into a distillation flask equipped with a heating mantle are charged a mixture of about 18.8 g 1-methoxy-2-propanol and 43.2 g of a biscarbamate as represented by the structure (MDI di (1-methoxy isopropanol) biscarbamate):

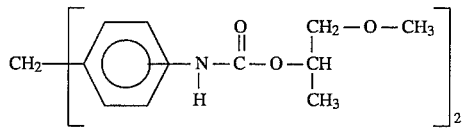

The mixture is heated under full vacuum to a temperature of less than 100° C., and 22.6 grams of the 2-hydroxy-3-methoxypropane distill off. This distillate is recovered in a cold trap. The material remaining in the distillation flask has a resinous appearance and appears to include an allophanate or polyurethane formed from the biscarbamate. In a second stage, the distillation flask is then heated to a temperature of about to 220° C., and a mixture of isocyanates and 1-methoxy-2-propanol begins to distill. The temperature of the distillate is about 140° to 180° C. The isocyanates condensed separately from the 1-methoxy-2-propanol and are recovered in a condensation flask upstream of the cold trap where the 1-methoxy-2-propanol is condensed. The isocyanates distilled from this have an NCO content of 22.4 percent, representing approximately 48 percent MDI and 52 percent of the monocarbamate. The distillation is continued until the distillation flask is empty except for a tarry residue which neither further decomposes or distils. This residue is recovered and found to weigh 1.6 g, which represents 4 percent of the initial mixture of biscarbamate and 2-hydroxy-3-methoxypropane.

A total of 21.3 g of a crystalline polyisocyanate containing 22 percent NCO groups is recovered. A total of 39.5 grams of 1-methoxy-2-propanol are recovered. This amount represents over 100 percent of theoretical, but upon examination it is seen that some MDI is present in the alcohol.

The isocyanates (20 g) recovered from the preceding pyrolysis are pyrolyzed a second time under the same conditions. The distillate obtained from this second pyrolysis has an NCO content of 32 percent, representing approximately 92 percent MDI and 8 percent monocarbamate. A tarry residue weighing only 0.3 g remains in the pyrolysis flask.

Examples 6–7 and Comparative Sample A

A series of MDI biscarbamates is pyrolyzed using the apparatus described in Example 5. In all cases, the pyrolysis is run under the same conditions as described in Example 5.

The weight of the starting biscarbamate, the recovered isocyanates, the recovered alcohol and tarry residue are as reported in Table 1.

TABLE 1

| Sample No. | MDI BIS-CARBAMATE | WT. BIS-CARBAMATE, g | WT. ISOCYANATE, g | WT. ALCOHOL g | WT. TAR, g (%)[1] |
|---|---|---|---|---|---|
| 6 | Di-3,3-dimethyl-2-butyl | 75.2 | 33.7 | 33.2 | 4.5 (5.9%) |
| 7 | Di-1-methoxy-2-propyl | 27.8 | 13.0 | 13.2 | 0.7 (2.5%) |
| A* | Diethyl | 30.2 | 5.3 | 10.2 | 13.7 (45.4%) |

[1] Based on the weight of the MDI biscarbamate starting material.
*Not an example of the invention.

As can be seen from the data in Table 1, the biscarbamates of this invention (Samples 6 and 7) form minimal tar when pyrolyzed in the absence of solvent. On the other hand, almost half of the MDI diethylbiscarbamate forms a tarry residue under these conditions.

Example 8

TDI di-1-methoxy-2-propyl biscarbamate (48.4 g), having the structure

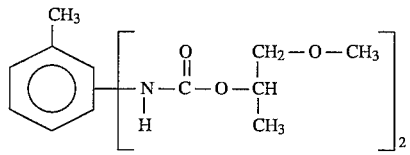

is pyrolyzed in an apparatus similar to that described in Example 8, at 180°–250° C. under 1 mm Hg vacuum. A distillate is collected at about 150°–160° C., weighing 34.5 g and having an NCO content of 17.2 percent. In a separate dry ice trap, 12.9 g of 1-methoxy-2-propanol is collected. The NCO content of the distillate indicates that it is predominantly the monocarbamate of TDI. The pyrolysis flask contains 0.85 g of tar, representing 1.8 percent of the weight of the starting material.

The distillate is then pyrolyzed again under the same conditions. This time, two distillates are collected-one at 75°–85° C. (predominately TDI) and one at 165°–175° C. (predominately the monocarbamate). The polymeric tar in the flask weighs less than 1 percent of the weight of starting material.

Example 9

H$_{12}$MDI di-1-methoxy-2-propyl biscarbamate (107.0 g) is pyrolyzed under the same conditions used in Example 5. The products of this pyrolysis are 41.9 g of a polyisocyanate having an NCO content of 26.6 percent, 55.1 g of 1-methoxy-2-propanol and 9.7 g tarry residue.

What is claimed is:

1. A polycarbamate as represented by the structure

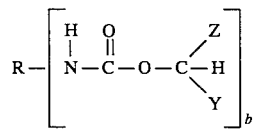

wherein b is a number of two or more, R is an organic radical with a valence equal to b, Y is a group having at least two carbon atoms, and Z is an aliphatic or aromatic group containing at least one carbon atom.

2. The polycarbamate of claim 1 wherein Z is a C$_1$–C$_4$ straight chain alkyl, C$_3$–C$_6$ branched alkyl, methoxy- or ethoxy-substituted C$_1$–C$_4$ alkyl, phenyl or benzyl group, and Y is represented by the structure —CR$^1$R$^2$R$^3$ wherein R$^1$ and R$^2$ are independently hydrogen, C$_1$–C$_6$ alkyl, aromatic, benzyl, alkoxy or phenoxy and R$^3$ is C$_1$–C$_6$ alkyl, aromatic, benzyl, alkoxy, phenoxy or dialkylamine.

3. The polycarbamate of claim 2 wherein R$^1$ and R$^2$ are hydrogen, and R$^3$ is C$_1$–C$_4$ alkoxy or phenoxy.

4. The polycarbamate of claim 3 wherein b is 2 and R is tolylene, dicyclohexylmethane or a diphenylmethane diradical.

5. The polycarbamate of claim 2 wherein R$^1$ is hydrogen, R$^2$ is methyl, ethyl or phenyl and R$^3$ is methoxy or ethoxy.

6. The polycarbamate of claim 5 wherein b is 2 and R is tolylene, dicyclohexylmethane or a diphenylmethane diradical.

7. The polycarbamate of claim 2 wherein R$^1$ and R$^2$ are each ethyl, methyl or phenyl and R$^3$ is methoxy or ethoxy.

8. The polycarbamate of claim 7 wherein b is 2 and R is tolylene, dicyclohexylmethane or a diphenylmethane diradical.

9. The polycarbamate of claim 4 wherein Z is methyl or ethyl, R$^3$ is methoxy, b is 2 and R is tolylene, dicyclohexylmethane or a diphenylmethane diradical.

10. A process for preparing a polyisocyanate, comprising pyrolyzing a polycarbamate represented by the structure

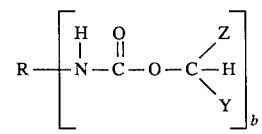

wherein b is a number of two or more, R is an organic radical with a valence equal to b, Y is a group having at least two carbon atoms, and Z is an aliphatic or aromatic group containing at least one carbon atom, under reduced pressure and at a temperature of about 150° to about 270° C., to form the corresponding polyisocyanate and alcohol.

11. The process of claim 10 which is conducted in the substantial absence of a solvent.

12. A process for preparing a polyisocyanate, comprising forming a polycarbamate represented by the structure

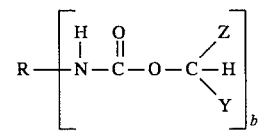

wherein b is a number of two or more, R is an organic radical with a valence equal to b, Y is a group having at least two carbon atoms, and Z is an aliphatic or aromatic group containing at least one carbon atom, and then pyrolyzing the polycarbamate under reduced pressure and at a temperature of about 150° to about 270° C. to form the corresponding polyisocyanate and alcohol.

13. The process of claim 12 wherein the pyrolysis is conducted in the substantial absence of a solvent.

14. A process comprising reacting a first polycarbamate represented by the structure

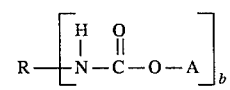

wherein A is C$_{1-6}$ linear alkyl, b is a number of two or more and R is an organic radical with a valence equal to b, with a secondary alcohol represented by the structure Z—CH(OH)—Y, wherein Y is a group having at least two carbon atoms, and Z is an aliphatic or aromatic group containing at least one carbon atom, at an elevated temperature such that a second polycarbamate represented by structure

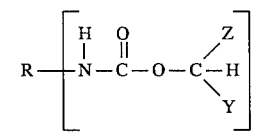

and an alcohol of the structure A—OH are formed, and wherein the alcohol A—OH is removed from the product polycarbamate continuously or intermittently as it forms.

15. The process of claim 14 wherein said elevated temperature is from about 100° C. and 250° C., and no organometallic catalyst is present.

16. The process of claim 14 wherein Z is a C$_1$–C$_4$ straight chain alkyl, C$_3$–C$_6$ branched alkyl, methoxy- or ethoxy-substituted C$_1$–C$_4$ alkyl, phenyl or benzyl group, and Y is represented by the structure —CR$^1$R$^2$R$^3$ wherein R$^1$ and R$^2$ are independently hydrogen, C$_1$–C$_6$ alkyl, aromatic, benzyl, alkoxy or phenoxy and R$^3$ is C$_1$–C$_6$ alkyl, aromatic, benzyl, alkoxy, phenoxy or dialkylamine.

17. The process of claim 15 wherein b is 2 and R is tolylene, dicyclohexylmethane or a diphenylmethane diradical.

18. The process of claim 17 wherein R$^1$ and R$^2$ are hydrogen and R$^3$ is methoxy or ethoxy.

19. The polycarbamate of claim 2 wherein R$^1$, R$^2$ and R$^3$ are all ethyl or methyl.

* * * * *